[19] Walkup et al.

[11] Patent Number: 5,071,754
[45] Date of Patent: Dec. 10, 1991

[54] PRODUCTION OF ESTERS OF LACTIC ACID, ESTERS OF ACRYLIC ACID, LACTIC ACID, AND ACRYLIC ACID

[75] Inventors: Paul C. Walkup, Richland; Charles A. Rohrmann, Kennewick; Richard T. Hallen, Richland; David E. Eakin, Kennewick, all of Wash.

[73] Assignee: Battelle Memorial Institute, Richland, Wash.

[21] Appl. No.: 468,704

[22] Filed: Jan. 23, 1990

[51] Int. Cl.$^5$ .......................... C12P 7/62; C12P 7/40; C12P 7/56
[52] U.S. Cl. .................................... 435/135; 435/136; 435/139; 560/179; 560/212
[58] Field of Search ............... 435/135, 136, 139, 853; 560/179, 212; 502/217

[56] References Cited

U.S. PATENT DOCUMENTS

| | | | |
|---|---|---|---|
| 1,123,920 | 1/1915 | Pollak et al. | 435/139 |
| 1,624,674 | 4/1927 | Pollak | 435/139 |
| 1,650,950 | 11/1927 | Matheson et al. | 560/212 |
| 1,993,089 | 4/1935 | Crawford et al. | 560/212 |
| 2,029,694 | 2/1936 | Bannister | 260/106 |
| 2,334,524 | 11/1943 | Wenker | 260/535 |
| 2,350,370 | 6/1944 | Schopmeyer et al. | 260/535 |
| 2,417,748 | 3/1947 | Hagemeyer, Jr. | 260/486 |
| 2,464,364 | 3/1949 | Atwood | 260/486 |
| 2,464,487 | 8/1951 | Filachione et al. | 260/484 |
| 2,790,822 | 4/1957 | Wolfram et al. | 260/465.9 |
| 2,811,545 | 10/1957 | Steadman | 260/486 |
| 2,850,240 | 11/1958 | Holmen | 260/486 |
| 3,022,336 | 2/1962 | Sennewald et al. | 260/486 |
| 3,087,962 | 4/1963 | Bortnick | 260/486 |
| 3,098,795 | 7/1963 | Kreps | 167/90 |
| 3,875,212 | 4/1975 | Ohrui et al. | 260/486 R |
| 3,914,290 | 10/1975 | Otsuki et al. | 260/486 R |
| 4,055,590 | 10/1977 | Gruber et al. | 560/179 |
| 4,464,539 | 8/1984 | Hashimoto et al. | 560/212 |
| 4,500,727 | 2/1985 | Kitamura et al. | 560/179 |

OTHER PUBLICATIONS

"Calcium compounds to Chloroamphenicol" Encyclopedia of Chemical Technology, Kirk–Othmer, vol. 4, pp. 14–27.
Filachione et al., "Lactic Esters by Reaction of Ammonium Lactate with Alcohols", vol. 44, Sep. 1952, p. 2189.
Filachione et al., "Preparation of Esters by Reaction of Ammonium Salts with Alcohols" Journal of the American Chemical Society, vol. 73, 1951, p. 5265.
E. J. Costello et al., "Preparation and Properties of Pure Ammonium DL-Lactate" Article dated Oct. 31, 1952.
Filachione et al., "Purification of Lactic Acid", *Indust. and Engineering Chemistry*, vol. 38, Feb. 1916, p. 228.
Burns et al., "Studies in Pyrolysis, Part I, The Pyrolysis of Derivatives of x-Acetoxypropionic Acid, and Related Substances" Article dated 12/17/34.

(List continued on next page.)

*Primary Examiner*—Douglas W. Robinson
*Assistant Examiner*—C. Geckle
*Attorney, Agent, or Firm*—Wells, St. Johns & Roberts

[57] ABSTRACT

Processes are disclosed for producing lactic acid, esters of lactic acid, acrylic acid, and esters of acrylic acid, primarily from fermentable carbohydrate materials. An overall process for producing esters of acrylic acid comprises: a) fermenting carbohydrate material with a lactic-acid-forming organism in the presence of $NH_3$ to produce ammonium lactate; b) combining the ammonium lactate with an alcohol; c) combining the ammonium lactate and alcohol with an effective catalyzing amount of gaseous $CO_2$ to catalytically esterify the ammonium lactate and alcohol into a lactic acid ester containing solution; d) recovering purified lactic acid ester; and e) vaporizing the lactic acid ester and passing it through a solid catalyst bed comprised of an effective catalyzing amount of crystalline hydrated and partially calcined calcium sulfate to catalytically convert lactic acid ester into an acrylic acid ester. Step "d" would be useful in a process for making low-cost, purified lactic acid. Similarly, step "e" would be useful in a process for making low cost, purified acrylic acid.

76 Claims, 3 Drawing Sheets

OTHER PUBLICATIONS

Ratchford et al., "Methyl Acrylate by Pyrolysis of Methyl Acetoxypropionate", Indust. and Engineering Chemistry, vol. 37 No. 4, Apr. 1945, pp. 382–387.

Smith et al., "Pyrolysis of Lactic Acid Derivatives", Industrial & Engineering Chemistry, Apr. 1943, pp. 473–479.

Fisher et al., "Methyl Acrylate Production", Industrial & Engineering Chemistry, vol. 36, No. 3, 3/1944, pp. 229–334.

Troupe et al., "Kinetics of Methanol–Lactic Acid Reaction" Industrial & Engineering Chemistry, vol. 42, No. 7, 1950, pp. 1403–1409.

Takeshita et al, "Recent Survey of Catalysis by Solid Metal", Catalysis Reviews, 8(1), 29–63 (1973).

Tanabe et al., "Catalytic Activity and Acidic Property of Solid Metal Sulfates", est. 1967.

Sharma, et al., "Esterification of Butanol with Propionic Acid Catalysed by Cation Exchange Resin", Chemical Indust. Developments, Incorp. CP&E, Jul. 1977, pp. 24–26.

Wiberg, *Laboratory Technique In Organic Chemistry*, McGraw-Hill Book Co., p. 214, 1960.

Kirk-Othmer, *Encyclopedia of Chemical Technology*, vol. 11, p. 891, 1966.

FIG. II

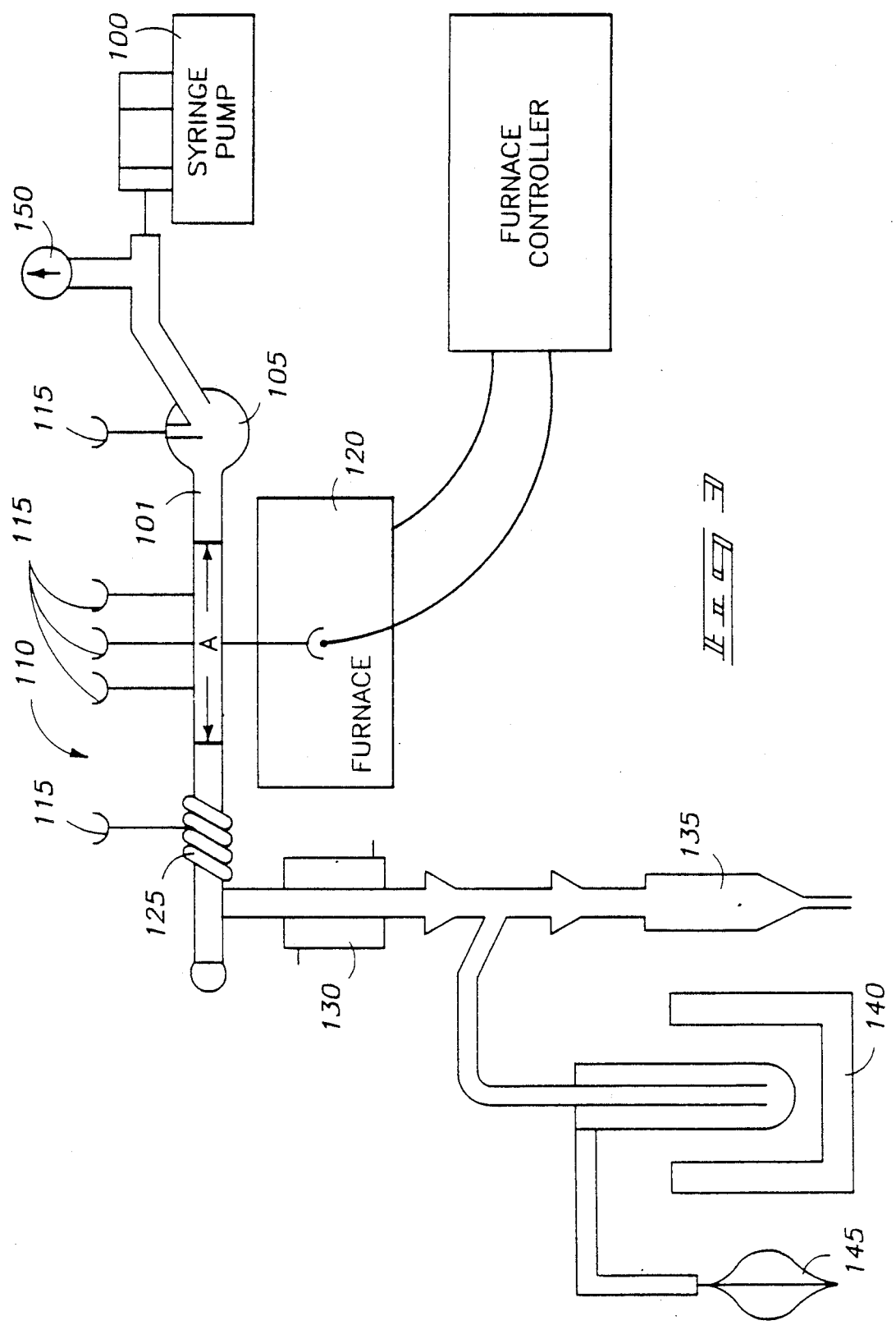

PRODUCTION OF ESTERS OF LACTIC ACID, ESTERS OF ACRYLIC ACID, LACTIC ACID, AND ACRYLIC ACID

TECHNICAL FIELD

This invention relates to processes for production of lactic acid, esters of lactic acid, and esters of acrylic acid, and acrylic acid, primarily from low cost fermentable carbohydrate material and ammonium lactate.

BACKGROUND OF THE INVENTION

The invention spawned from research for economical processes for the conversion of low valued carbohydrates to higher valued products other than ethanol. Low valued carbohydrates, in many cases considered annoying waste products today, come from a number of sources that include molasses, food production wastes, wood or cellulosic wastes, etc.

The research first addressed the production of esters of acrylic acid, and particularly production of alkyl acrylate esters from black-strap molasses, a large volume waste product of the sugar cane industry. The first processes involved dehydration of lactate esters (i.e. removal of a hydroxyl group and hydrogen and forming a water molecule) to form acrylate esters, and involved fermentation technology for production of the lactate esters.

The acrylate products have a firm position in the marketplace for industrial coatings, water based emulsion-type paints for interior as well as exterior applications, and for plastic sheeting and films. The production of acrylates is a mature industry that has involved the petrochemistry of materials such as acetylene, ethylene cyanhydrin, acrylonitrile and propylene. Processes based on the oxidation of propylene are dominant today. Propylene is a coproduct for some major processes for the production of ethylene. However, some important ethylene processes yield no propylene at all. Furthermore, there are no major production processes that are operated to produce propylene as the major product. Thus, propylene varies widely in its price and availability. Its inherent close alignment with the petrochemical industry generally, and with ethylene in particular, creates rather uncertain and unstable economics.

Lactic acid is now produced commercially in the United States essentially only from acetaldehyde and hydrogen cyanide. On the other hand, there is much low cost carbohydrate material that is anticipated to assure a stable and long term supply if efficient, economic processes could be developed for converting this material into lactic acid, esters of lactic acid, acrylic acid, or esters of acrylic acid. Such processes will most likely entail the fermenting of the carbohydrate material with a lactic acid forming organism. Up to this time, essentially all commercial processes of fermentation to produce lactic acid have involved calcium carbonate as the means for maintaining pH at high enough levels to maintain the continuous activity of the fermentation organism. However the resulting salt, calcium lactate, has a limited solubility. To assure that the fermentation liquor is maintained as a pumpable fluid, the presence of a large fraction of solid hydrated calcium lactate must be avoided. This necessitates overall fermentation operations on rather dilute levels.

U.S. Pat. No. 2,565,487 to Filachione et al. and an article entitled "*Lactate Esters by Reaction of Ammonium Lactate With Alcohols,*" by Filachione et al. disclose the use of $NH_3$ in a fermentation process to produce ammonium lactate, with subsequent conversion to lactate esters. These processes use $NH_3$ for pH control. The ammonium lactate which is produced is subsequently converted to an ester by prolonged heating in the presence of a large excess of butanol or higher alcohol at atmospheric pressure. Reaction times are stated to take from 5 to 10 hours, with as much as 17 hours being required. Even then, the percentage yields are not very great.

Furthermore, although the Filachione et al. patent states in one instance that methyl or ethyl alcohols are useable, they also state that the higher boiling alcohols are more suitable to the reaction than lower boiling alcohols. It would be advantageous to develop a process that could utilize either high boiling or low boiling alcohols for conversion of ammonium lactate to a lactic acid ester. It would further be preferable to develop a process which requires a significantly reduced reaction time, and results in higher conversion to the lactate ester.

The production of an acrylic acid ester from a lactate ester would at first glance seem to require simply removing a hydroxyl group and hydrogen atom from adjacent carbon atoms to result in formation of the acrylic acid structure. However, other reactions are dominant and largely inhibit this conversion to an acrylate. The principal competing reaction is formation of self reaction products, such as lactides, which are subsequently more readily decomposed into fragments such as carbon monoxide, acetaldehyde, and water.

Prior art techniques to avoid this involve formation of intermediates which impair lactide production, and by the use of certain catalysts to promote the direct removal of H and OH from the lactate ester. For example, U.S. Pat. No. 2,859,240 to Holmen discloses a number of catalysts useful in a process conducted at between 250° C. to 550° C. to produce the acrylate.

Aspects of the following invention would also be useful in the production of purified lactic acid. Lactic acid may be a suitable feed material for the production of biodegradable plastics. The polystyrene and polyethylene plastics of this day have wide use because of their low cost and desirable properties. However, they create horrendous disposal problems. Processes for the production of biodegradable lactic acid polymers are being developed, but the cost of producing a high quality commercial grade of lactic acid may make the resulting plastic prohibitively expensive. This problem could be overcome by an efficient, low cost production of lactic acid from low-cost carbohydrate materials.

BRIEF DESCRIPTION OF THE DRAWINGS

Preferred embodiments of the invention are illustrated in the accompanying drawings, in which:

FIG. 3 is a diagrammatic view of testing equipment used in examples described below in the specification.

DETAILED DESCRIPTION OF THE PREFERRED EMBODIMENTS

The following disclosure of the invention is submitted in furtherance with the constitutional purpose of the Patent Laws "to promote the progress of science and useful arts" (Article 1, Section 8).

The invention comprises any one or more of, a) a method of producing lactic acid from ammonium lactate;

b) a method of producing lactic acid from fermentable carbohydrate materials;

c) a method of producing esters of lactic acid (lactate esters) from ammonium lactate;

d) a method of producing esters of lactic acid (lactate esters) from fermentable carbohydrate materials;

e) a method of producing esters of acrylic acid (acrylate esters) from lactic acid esters;

f) a method of producing esters of acrylic acid (acrylate esters) from fermentable carbohydrate materials.

g) a method of producing acrylic acid from esters of lactic acid (lactate esters); and h) a method of producing acrylic acid from fermentable carbohydrate materials.

The invention is expected to be useful for the production of lower cost concentrated lactic acid, lactate esters, acrylic acid, and acrylate esters from crude ammonium lactate fermentation liquors. In those applications for the production and purification of lactate esters, acrylate esters, and acrylic acid, the direct production of the intermediate lactic acid can be avoided.

It is anticipated that any of a wide variety of fermentable carbohydrate materials will be usable as feed materials in accordance with the invention to produce ammonium lactate fermentation liquors. Furthermore, certain aspects of the invention as claimed have applicability to ammonium lactate solutions independent of whether the ammonium lactate was obtained from a fermentation process. Purified lactic acid, producible in accordance with one aspect of the invention, may provide a suitable basic raw material useful for producing biodegradable polymers that have yet to be developed by the patentee or others.

Figure 1:
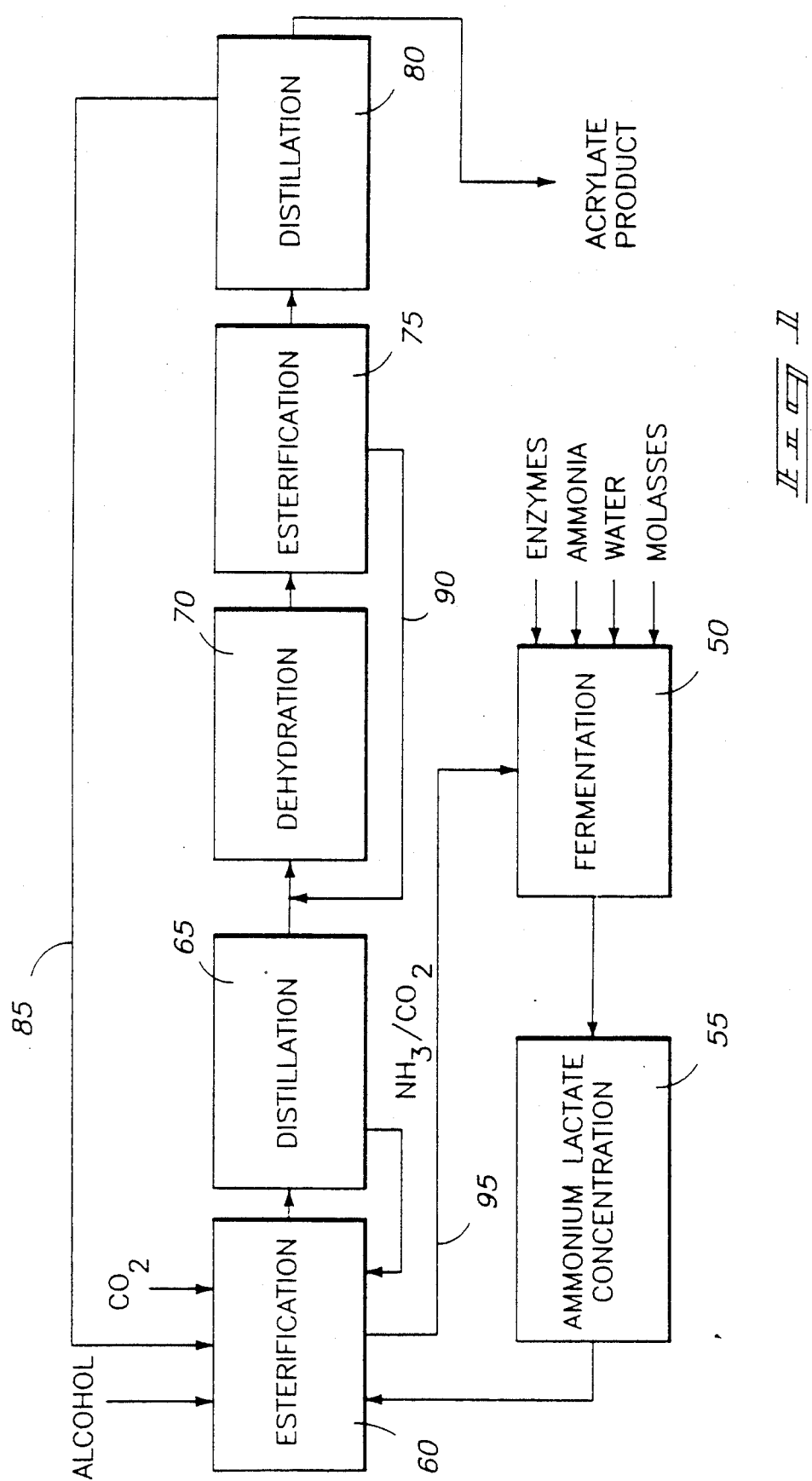
FIG. 1 is a schematic flow chart of an overall process for conversion of low cost carbohydrate material into a higher valued acrylate product in accordance with the invention.

The discussion proceeds with reference to FIG. 1 and an overall method of producing esters of acrylic acid from fermentable carbohydrate materials.

As illustrated, the overall method starts with fermentation and concentrating steps 50, 55 to produce an ammonium lactate solution. This ammonium lactate solution is combined with an alcohol and $CO_2$, and esterified in step 60 to produce a lactic acid ester containing solution. After concentrating this solution (step 65), a hydrogen atom and hydroxyl group are removed from the lactic acid ester in step 70 to produce an acrylic acid ester (an acrylate). Step 70 may also produce acrylic acid and lactic acid which are subsequently esterified in step 75. The acrylate is concentrated or purified in step 80 to produce an acrylate product stream.

Fermentation

The first step of this overall process in accordance with the invention is to ferment a carbohydrate material with a lactic acid forming organism in the presence of $NH_3$ to produce ammonium lactate. It is indicated generally by the representation below.

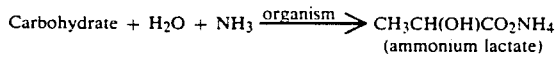

Any suitable carbohydrate material that would produce lactic acid in the presence of a lactic acid producing organism is anticipated to be usable in accordance with the invention. One such carbohydrate material would be black-strap molasses. Sugar cane juice, sugar beet juice, potato processing wastes, whey, hydrolyzed wood or various other carbohydrate materials could also be used. Fermentation could be conducted by use of known prior art process that use $NH_3$, or by a preferred process described immediately below.

As a first step in such a process, black-strap molasses containing about 50% sucrose is diluted with water to about 30% sugar by weight. The solution may then be hydrolyzed, such as with enzymes as represented in FIG. 1. Hydrolysis of the solution with enzymes or acid ($H_2SO_4$) to convert the carbohydrate to monosaccharides has been shown to be beneficial to subsequent fermentation. The hydrolysis method would depend on the feed material, and would be generally known by people of skill in the art. For example, starch can be converted with a combination of α-amylase and glucosidase. Cellulose can be converted with cellulase or by acid hydrolysis. Disaccharides such as sucrose can be converted with glucosidase or possibly with yeast at a temperature high enough to inhibit ethanol production.

The diluted and hydrolyzed solution is fermented at about 35° C. to 55° C. in the presence of an *Acidophilus bacterium*, which is active at this temperature, and $NH_3$. Preferred species are *Lactobacillus delbruckii* and *Lactobacillus bulgaricus*. The temperature is controlled, and the pH maintained at about 5 by addition of $NH_3$. The Lactobacillus changes the monosaccharides into lactic acid or lactate salts. The fermentation product of step 50 under these conditions will be ammonium lactate, as the *Lactobacillus bacterium* essentially produces no other fermentation products. A high yield, perhaps as high as 95%, is expected.

The crude solution of ammonium lactate is then concentrated by any of a variety of ways, such as evaporation, solvent dewatering, absorption, and the like (Step 55).

Ammonium lactate has essentially no solubility limit in aqueous solutions, and thus permits fermentation to proceed up to concentrations at which point the activity of the fermentation organism is impaired. Experience indicates that this is at a concentration of about 30% by weight, although higher concentrations might be possible. By this method of operation, energy savings are achieved since less water needs to be removed for the further processing steps. The process is anticipated to be most favorable for fermentation of low-cost highly concentrated sugar sources such as molasses.

Alternate fermentation processes could of course be used. In one such process, the fermentation could be conducted first utilizing a yeast at a lower temperature to produce an alcohol, such as ethanol. A second fermentation would be conducted with the lactobacillus at a higher temperature, as described above, to produce ammonium lactate. Conventional evaporation and distillation would then be used to concentrate the ammonium lactate and recover the ethanol for use in downstream process steps, described below, for production of ethyl lactate as either an intermediate or end product.

In such a process, a final product of ethyl lactate or ethyl acrylate would be derived entirely from the fermentation of the carbohydrate material.

Esterification

Referring again to FIG. 1, esterification of the ammonium lactate to a lactic acid (lactate) ester occurs in a step 60. Here, the ammonium lactate from step 55 is mixed with an alcohol and an effective catalyzing amount of gaseous $CO_2$ to produce a reaction mixture. The reaction mixture is maintained under a reaction mixture pressure and at a reaction mixture temperature for a period of time so as to catalytically esterify the reaction mixture into a lactic acid ester containing solution.

The expected operable range of the reaction mixture pressure is from approximately 1 atmosphere to 200 atmospheres, and should be sufficient to maintain the ammonium lactate and alcohol in the reaction mixture in the liquid phase. The preferred range for the reaction mixture temperature is from approximately 100° C. to 200° C., with 160° C. to 180° C. being most preferred. The predetermined period of reaction time is anticipated to be less than or equal to two hours.

The preferred range for the molar ratio of alcohol to ammonium lactate in the reaction mixture is from 1:1 to 10:1, with the effective amount of $CO_2$ being defined by a partial pressure of $CO_2$ in the reaction mixture of from approximately 1 atmosphere to 200 atmospheres.

The preferred alcohol is selected from the group consisting of alcohols such as methanol, ethanol, propanol, and isopropanol primarily due to lower cost, and herein lies one major advantage of this aspect of the invention. The invention is also anticipated to be workable with alcohols having four or more carbon atoms. The lactate ester produced will typically be an alkyl lactate having the same alkyl group as the alcohol. Methanol is the preferred alcohol in the context of the above described step for economic reasons.

The conversion of ammonium lactate and an alcohol to a lactic acid ester in the presence of $CO_2$ is indicated generally by the equation:

$$CH_3CH(OH)CO_2NH_4 + ROH \xrightarrow{CO_2} CH_3CH(OH)CO_2R + NH_4OH$$

where R is a hydrocarbon group.

Esterification of ammonium lactate and an alcohol in the past has been found to be impractical for the lower alcohols, i.e. methanol and ethanol. (see U.S. Pat. No. 2,565,487 to Filachione et al.) However, use of an effective catalyzing amount of gaseous $CO_2$ enables lower alcohols to be used very effectively to obtain high percentage yields, and is also anticipated to be an improved process with alcohols higher than ethanol.

The conversion of ammonium lactate to the alkyl lactate is understood to occur by two reactions. By way of example, these are indicated below for ammonium lactate and methanol to produce methyl lactate. In the first reaction, ammonium lactate is converted to $NH_3$ and lactic acid. In the second reaction, the lactic acid is esterified with methanol to produce methyl lactate. Both reactions are reversible and can be represented by equilibrium constants ($K_{eq}$).

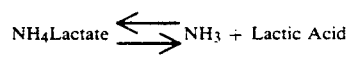

$$K_{eq} = \frac{(NH_3)(\text{Lactic Acid})}{(NH_4\text{Lactate})}$$

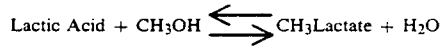

$$K_{eq} = \frac{(CH_3\text{Lactate})(H_2O)}{(\text{Lactic Acid})(CH_3OH)}$$

To better understand which reaction limits methyl lactate yield, equilibrium constants were determined for both reactions.

The equilibrium constant for the second reaction, esterification of lactic acid, was determined by performing laboratory experiments. Two separate experiments were performed. In the first, 88% lactic acid was reacted with a 10 fold excess of methanol. At equilibrium, 97% of the lactic acid was converted to methyl lactate as determined by gas chromatography. Using this number, $K_{eq}$ was calculated to be 4.0. In the second experiment, methanol, water, and methyl lactate were reacted until equilibrium was reached. At equilibrium, 96% of the methyl lactate remained. Using this number, $K_{eq}$ for the second reaction was calculated to be 3.9. This value of $K_{eq}$ means the equilibrium favors formation of products (methyl lactate).

$K_{eq}$ for the second reaction and the results from the previous experiments enabled computation of $K_{eq}$ for the first reaction. This $K_{eq}$ constant was calculated to be 0.1. This small value indicates that the equilibrium favors the reactants (ammonium lactate). These results further show that the yield of methyl lactate, and other lactates by analogy, is limited by the conversion of ammonium lactate to lactic acid and $NH_3$. To increase methyl lactate yields, the first reaction must be shifted towards the products. This will occur with the removal or reaction of the $NH_3$ that is released from the ammonium lactate. The $CO_2$ effectively does this by reacting with $NH_3$. Surprisingly, the $CO_2$ in solution also provides sufficient acidity to catalyze the formation of the ester.

The Filachione et al. patent teaches the use of ammonium sulfate as an esterification catalyst for an alcohol-ammonium lactate solution. Our experiments indicated this to be the least effective catalyst. Other catalysts were tested, such as potassium pyrosulfate ($K_2S_2O_7$) and an ion exchange resin, that were more effective than ammonium sulfate. However these catalysts would have costly regeneration or recovery processes which may significantly impair their practical use in a commercial process. For example, a process using ion exchange resin would require the consumption of acid to regenerate the acid form of the resin and liberate $NH_3$. $K_2S_2O_7$ would react with water to produce $2KHSO_4$, which will react with $NH_3$ to produce potassium ammonium sulfate, $KNH_4SO_4$. $K_2S_2O_7$ would be regenerated and $NH_3$ recovered by calcining $KNH_4SO_4$. However even here, the yield using $K_2S_2O_7$ at 170° C. is expected to be low as compared with the use of $CO_2$.

The results of testing these catalysts at various temperatures are presented in Table 1 below.

TABLE 1

Effects of Additives on Esterification of Ammonium Lactate

| Run | Additive | Time (hr) | % Yield |
|---|---|---|---|
| | Reaction Temperature 130° C. | | |
| 1 | None | 1.5 | 13.8 |
| 2 | $(NH_4)_2SO_4$ | 1.5 | 12.1 |
| 3 | $K_2S_2O_7$ | 1.5 | 34.6 |
| 4 | Ion Exchange Resin | 1.5 | 49.8 |
| | Reaction Temperature 150° C. | | |
| 5 | None | 1.5 | 30.0 |
| 6 | $K_2S_2O_7$ | 1.5 | 49.0 |
| 7 | $K_2S_2O_7$ | 2.5 | 64.9 |
| 8 | Ion Exchange Resin | 1.5 | 60.2 |
| | Reaction Temperature 170° C. | | |
| 9 | None | 1.5 | 47.6 |
| 10 | $K_2S_2O_7$ | 1.5 | 59.9 |
| 11 | $K_2S_2O_7$ | 2.5 | 49.4 |
| 12 | Ion Exchange Resin | 1.5 | 79.9 |

The evaluation of these catalysts was conducted in small autoclaves with minimal vapor space at the indicated temperatures. The containers were continuously shaken throughout the test to assure contact between the alleged catalyst and the reactants. The analytical results as to yield percentages were obtained by gas chromatography.

Figure 2:
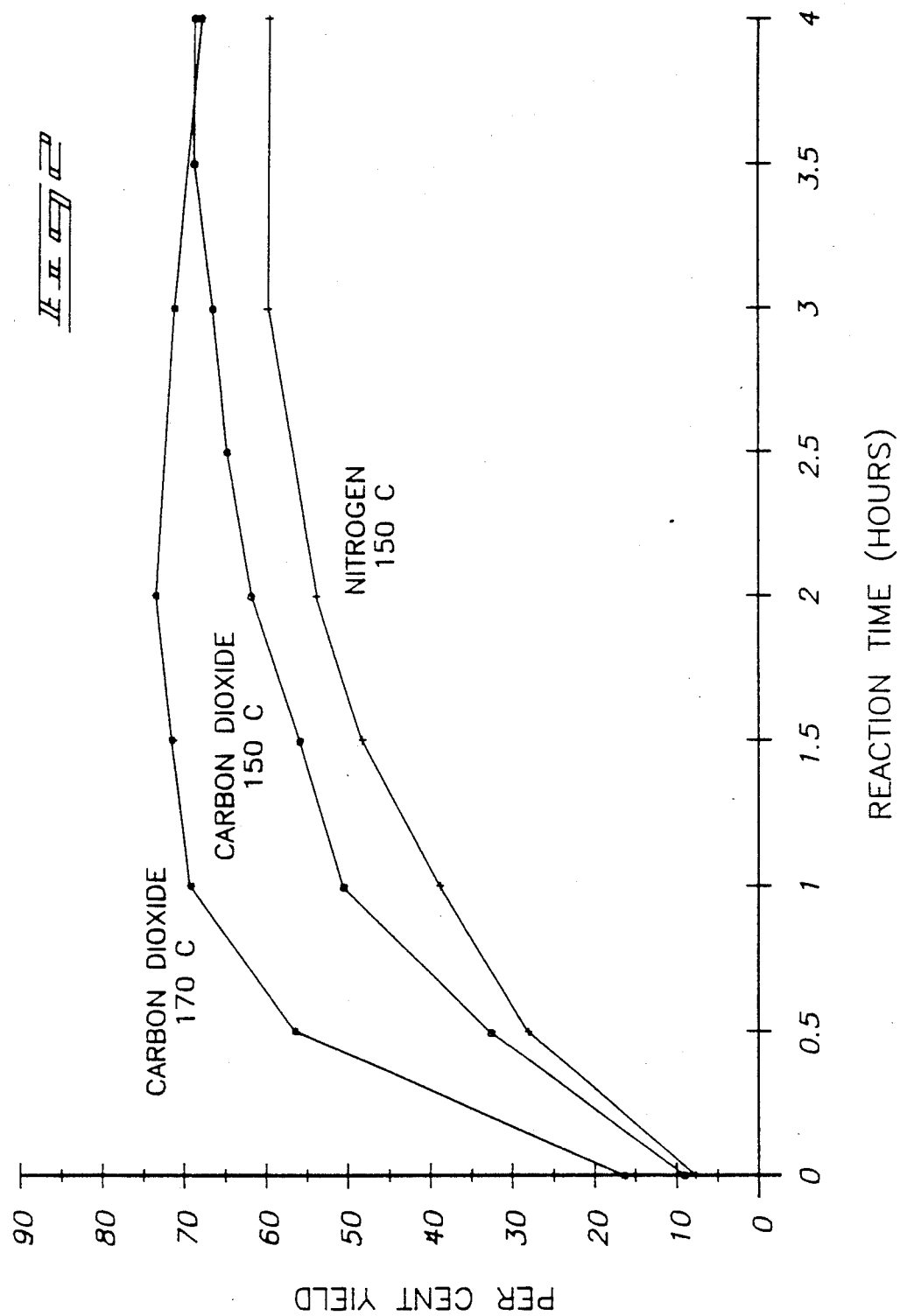
FIG. 2 is a graph of percentage yield versus reaction time for a method of producing an ester of lactic acid from ammonium lactate in accordance with the invention.

Experiments were also conducted using pressurization alone with nitrogen as an inert cover gas, and with $CO_2$. These results are indicated in FIG. 2. Although pressure alone in the presence of nitrogen is indicated as being somewhat effective, $CO_2$ is clearly superior in assuring rapid achievement of equilibrium and high yields.

The results of these pressurization experiments were obtained with one liter of liquid with continuous stirring, and equipment was provided for periodic sampling of both the liquid and gas phases. The procedure for the one-liter autoclave experiments involved placing 500 ml of methanol and 50 g of ammonium lactate solution in the autoclave at room temperature, and pressurizing the autoclave with the nitrogen or $CO_2$ to about 700 psig. The furnace surrounding the autoclave was then energized. When the appropriate temperature was attained in the autoclave, a sample was taken. At this point the pressure was in the range of about 950 psig to 2240 psig, varying among the experiments as indicated in Table 2 below. This point was taken to be the starting time, or time zero, as illustrated in the graph of FIG. 2. By way of example, it required approximately one hour of heating to reach 150° C. from room temperature to reach time zero.

TABLE 2

| | Temp | Cold Pressure (psig) | Initial Hot Pressure (psig) | Highest Pressure During Run (psig) |
|---|---|---|---|---|
| $CO_2$ | 150 | 673 | 2236 | 2109 |
| $CO_2$ | 170 | 673 | 1439 | 1439 |
| $N_2$ | 150 | 700 | 950 | 1000 |

Periodic sampling was conducted, and percentage yield analysis obtained by gas chromatography. The results clearly indicate that the use of $CO_2$ and pressure in the range of 700 psig to 2240 psig is preferred. The reaction conducted at 170° C. and at a pressure in the range of 700 psig and 1440 psig required less than two hours to reach equilibrium. In another experiment in which the carbon dioxide was continuously flushed through the reaction vessel at a temperature of 150° C. and at a pressure in the range of 700 psig to 860 psig, the yield of the ester was unchanged compared to the static experiments. This result suggests that somewhat lower pressures may be successfully used. The preferred pressure range is believed to be between 1 and 200 atmospheres.

A practical process is thereby achievable with a reaction time of only 1.5 hours to reach near equilibrium levels. Such a process would require neither filtration to recover a solid catalyst nor calcination to regenerate a catalyst. $NH_3$ and $CO_2$ could be recovered by stream 95 (FIG. 1) as gases for recycle, as is more fully described below. Equilibrium yields of the lactate should be about 75%, and therefore a single recycle of residues should assure process yields of over 90%. There was a concern that such thermal processing of lactates or lactic acid would form nonreactive polymers which would prevent the achievement of high yields. However, analytical examination of the reacted mixture from this method of esterification showed no production of such polymeric residues.

A possible explanation of the mechanism of $CO_2$ in the above process may stem from $CO_2$ and aqueous $NH_3$ forming a rather unstable compound (ammonium bicarbonate, $NH_4HCO_3$). $NH_4HCO_3$ decomposes at approximately 60° C. at atmospheric pressure. Further, ammonium lactate itself is rather unstable as evidenced by the odor of $NH_3$ over heated, concentrated, ammonium lactate solutions. Excess $CO_2$ at pressure in the process of the invention probably makes the ammonium bicarbonate more stable at higher temperatures, and shifts the equilibrium toward the ammonium bicarbonate salt. Thus, the more stable bicarbonate plus excess $CO_2$ may be allowing more $NH_3$ to evolve from the unstable ammonium lactate, and leave more lactate ions for reaction with the alcohol to form the ester. Higher pressures and temperatures are anticipated to accelerate these reactions.

The optimal full scale reactor for this process step has not been demonstrated but is expected to be of the continuous, tubular reactor type.

It will be readily apparent that the esterification reaction in the presence of $CO_2$ is clearly operable regardless of the overall described process, and the source of ammonium lactate.

$NH_3$ and $CO_2$ Recycle

Referring again to FIG. 1, off gas stream 95 from step 60 is an $NH_3/CO_2$ recycle or recovery stream. Depending upon the scale of operations, the complexities and costs for recycle may not be justified. Furthermore even for large scale operations, $CO_2$ recycle may not be justified since in some cases waste flue gases may be used directly as the source of $CO_2$. In any event, it is expected that $NH_3$ will be recovered.

Off gas stream 95 may contain some quantities of water, alcohol, and the lactate which was produced by esterification step 60. Furthermore, there may be a tendency for the $NH_3$ and $CO_2$ in the recycle stream to form objectionable solid ammonium carbonate or bicarbonate. The following are alternative example processes for treating the vent gases of stream 95.

At the first step in any of these processes, the vent gas would be slightly lowered in pressure from esterification step 60 preferably to approximately two atmospheres, and preferably cooled to slightly above about 60° C. It is preferable to maintain the vent gases at least about 60° C. to prevent formation of solid ammonium carbonate or bicarbonate. At these temperatures, the carbonates are essentially completely decomposed into their gaseous components. Also under these conditions, essentially all of the alcohol, water, and the lactate in the vent gas will be condensed. The condensate would be delivered back to the FIG. 1 process product stream just upstream of distillation step 65 (also described below) for separation, recovery and purification. The vent gases from which the liquids have been recovered as above are expected to consist of $NH_3$ and $CO_2$, with only negligible amounts of water, alcohol, and lactate ester.

In the first alternative process, the above treated vent gas while still at above about 60° C. and now at essentially atmospheric pressure would be delivered through intermediate storage to the fermenter where the $NH_3$ is re-utilized to produce ammonium lactate. With this process, the fermenter would preferably be enclosed to provide the means for recovering the $CO_2$ for recycle to esterification step 60. $CO_2$ is not anticipated to have any adverse effects on the fermentation process.

In the second alternative process, the treated vent gas at slightly above 60° C. and at slightly above atmospheric pressure would be contacted with a solution of potassium carbonate/bicarbonate in which the $CO_2$ would be effectively absorbed. The $NH_3$ would be released essentially free of $CO_2$ for recycle. With this process, the fermenter would not necessarily have to be enclosed, with the $NH_3$ being injected near the bottom of the fermenter. The potassium bicarbonate solution would then separately be heated to above about 100° C., under which conditions the $CO_2$ is released for collection and recycle. The potassium carbonate absorption process has been used commercially on a large scale to recover pure $CO_2$ from flue gases for dry ice manufacture, or for use as a cover gas in the processing of combustible liquids. It could also serve as the means for recovering $CO_2$ from flue gases to provide make-up gas for this process.

In the third alternative process, the treated vent gas would be contacted with a regenerable amine (such as mono-ethanolamine) for $CO_2$ separation recovery. Amines are used on a very large scale commercially for acid-gas ($CO_2$) treatment, such as for purifying hydrogen from $NH_3$ plant shift-gas converters. By selection of the specific amine and acceptable temperature conditions, this process should be suitable for separation of $NH_3$ and $CO_2$ for recycle as in the above process.

In each of the three alternative process, it is preferable to maintain the $CO_2$ and $NH_3$ in the gaseous state to prevent the formation of solid ammonium carbonate or bicarbonate. A preference for either of the three alternatives described above would favor the one most effective in recovering $NH_3$ at the least cost and with the minimum complexity.

Lactic Acid Ester to Acrylic Acid Ester Conversion

Referring again to FIG. 1, the lactic acid ester containing solution from step 60 is next treated, by a conventional vacuum fractional distillation step 65, to remove water, to recycle unreacted alcohol and lactic acid, and to concentrate and purify the lactate acid ester. The overhead concentrated lactic acid ester at this point could be withdrawn and utilized in other processes, or treated further in accordance with other aspects of the invention that follow. The bottoms stream would be recycled to esterification step 60 after removal of residual solids.

The lactic acid ester (lactate ester) can be converted into an acrylic acid ester (acrylate ester) in accordance with another novel aspect of the invention. The acrylate is formed from the lactate by catalysis which removes a hydroxyl group and adjacent hydrogen atom to form the acrylate double bond. The hydroxyl and hydrogen combine to form water. This is indicated in FIG. 1 as step 70, which is labelled "Dehydration". The general reaction is indicated by the equation below:

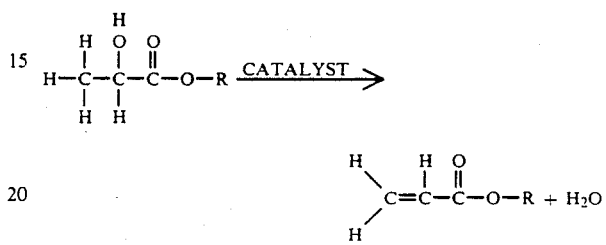

The selection of an operable catalyst is important because conversion levels, reaction rates, selectivity and catalyst life can each profoundly affect the process economics in terms of plant/equipment costs, as well as related operating costs and raw material consumption.

In accordance with the invention, a solid catalyst bed comprising an effective catalyzing amount of crystalline hydrated and partially calcined calcium sulfate has been determined to be the preferred catalyst. The lactic acid ester from esterification step 60, and purified by step 65, is vaporized and passed through such a catalyst bed to effectively convert the lactic acid ester into an acrylic acid ester. The vaporized lactic acid ester and solid catalyst bed are maintained in contact at a contact temperature and a predetermined contact pressure for a residence time. The crystalline hydrated calcium sulfate of the catalyst bed is preferably prepared by partially calcining it at or above the contact temperature. The contact temperature is preferably from about 350° C. to 410° C. The contact pressure is preferably substantially atmospheric. Under such conditions, the residence time should be less than or equal to 30 seconds.

The solid catalyst bed further preferably comprises an additive selected from the group consisting of buffering agents and promoters. It is preferably present in an amount from approximately five to twenty five weight percent of the solid catalyst bed. The buffering agents and promoters are preferably selected from the group consisting of calcium carbonate, calcium metaphosphate, calcium orthophosphate, calcium pyrophosphate, potassium dihydrogen orthophosphate, and sodium monohydrogen orthophosphate.

A system which was used for testing various catalysts is illustrated in FIG. 3. The liquid feed material used was methyl lactate which was accurately metered and injected by a syringe pump 100, as shown. An evaporation pot 105 is provided to allow the methyl lactate to vaporize before passage through a catalyst bed 101 of a reactor tube 110. Numerous thermocouples 115 were provided to monitor temperature conditions in various portions of the apparatus. The illustrated furnace 120 and heat tape 125 provided the necessary heat for the system. The samples were collected by means of a cooling condenser 130, product collection flask 135, dry ice trap 140, and a gas collection bag 145, as is more fully described below.

Methyl lactate was injected by syringe pump 100 and vaporized in evaporation pot 105. The gas then flowed through catalyst bed 101, which was held in a horizontal position. The tested catalysts were confined within reactor 110 in the space indicated by letter "A" of bed 101. Care was required in packing catalyst particles into area "A" to avoid channeling of the vapor, and to ensure uniform contact between gas and catalyst. Feed rates, catalyst volume and catalyst vessel dimensions were adjusted to maintain a fixed vapor velocity. The prepared catalyst size range was from $-\frac{1}{4}$ inch to $+\frac{1}{8}$ inch, having a 70% void volume based upon water displacement.

The vapor from the catalyst bed flowed through cooling condenser 130. Liquid was collected in a product collection flask 135, while the remaining uncondensed gas flowed to dry ice trap 140, and ultimately to Kelvar TM gas collection bag 145.

Most experiments were performed at atmospheric pressure, as monitored by pressure gauge 150. The addition of a vacuum pump (replacing gas collection bag 145) enabled experiments at subatmospheric pressure. The use of a controlled displacement diaphragm pump (instead of syringe pump 100), and the addition of a pressure throttling valve downstream of reactor 110, enabled experiments at elevated pressure.

Product samples were serially collected after a fixed amount of feed injection. Each product sample was routinely analyzed by use of a Hewlett Packard model 5830A gas chromatograph, equipped with a glass column (six feet by one-quarter inch) containing 10% SP-1200 (SP-1200 is a trademark of Supelco, Inc.) with 1% phosphoric acid. Other standard analytical techniques, including mass spectroscopy and NMR spectroscopy were used as necessary to confirm standard purity and to identify byproducts.

A variety of materials were tested as catalysts and included, tungsten oxide, chromium oxide, silica molybdenum oxide, rhenium oxide, vanadium pentoxide, magnesium oxide, nickel oxide, zirconium oxide, calcium phosphates, barium phosphates, magnesium phosphate, bismuth phosphate, cobalt oxide, lithium aluminate, calcium sulfate, calcium carbonate, proprietary commercial molecular sieves, barium sulfate, strontium sulfate, lanthanum phosphate, barium fluoride, barium chloride, aluminum phosphate, zinc sulfate, calcium metasilicate, calcium zirconate, calcium titanate, calcium stannate, calcium aluminate, strontium carbonate, magnesium carbonate, calcium selenite, calcium borates and nickel sulfate. These materials were used alone, or as mixtures with others and promoters, and supported on extended surface materials such as alumina, silica gel, graphite and agents such as sodium and potassium mono and dihydrogen phosphates or organic agents such as phenothiazine.

Based on the experiments, the preferred catalyst by far was a specially prepared calcium sulfate having an additive of buffering agents and promoters. The remaining candidates tested were inferior or ineffective. Operation at either above or below atmospheric pressure was shown to be effective, but without any appreciable benefits.

The preferred method for preparing a calcium sulfate for a catalyst bed for use in accordance with the invention is by first dry mixing and grinding any additives with the calcium sulfate. Preferably any buffers or promoters (additives) are intensively dry mixed and ground with the particular calcium sulfate, before the addition of water, in order to produce a catalyst of sufficient hardness and activity for practical use. Water in then combined with the dry mixed material to a molar ratio of water to calcium sulfate of from approximately 1.5:1 to 3.0:1 to produce a hydrated mixture. Next, the hydrated mixture is allowed to dry and harden into a set hydrated mixture.

The set hydrated mixture is crushed into a crushed hydrated mixture, and calcined at a temperature greater than or equal to approximately 350° C. for a sufficient period of time to only partially dehydrate the crushed hydrated mixture. It is believed that the catalyst activity derives from the fact that calcium sulfate dihydrate, as exemplified by gypsum, has a layered crystal structure. The layers are bound together by water molecules, each of which is bonded to a calcium ion and an oxygen atom of one layer and an oxygen atom of the adjacent layer. This structure is thought to be retained after partial calcining. This leaves active sites for bonding to lactate hydrogen atoms. Hydrogen bonding at these sites explains the dehydration activity.

Also, the partially calcined calcium sulfate material in accordance with the invention can be preferably exposed to $SO_3$ at a temperature of about 330° C. for a period less than or equal to five hours. This treatment was discovered to improve the catalyst performance.

An example catalyst was prepared by calcining calcium sulfate dihydrate which was formed by mixing calcium sulfate half hydrate (Plaster-of-Paris) with about 30% by weight water, and allowing the mixture to harden into the dihydrate cement-like form. In another successful catalyst, the above analytical grade calcium sulfate-half hydrate (from Specialty Chemical Division-Allied Chemical-Baker and Adamson Products, Morristown, NJ) was used with water in which 6% by weight of 2:1 molar ratio of $Na_2HPO_4$ and $KH_2PO_4$ was dissolved. These serve as buffering agents which contribute to extending the life of the resulting catalyst. Successful catalyst compositions were also made using high purity calcium sulfate half hydrate (Thin Layer Chromatography Grade Calcium Sulfate Half Hydrate, from the J. T. Baker Chemical Co.), with promoters such as calcium metaphosphate dry mixed with the calcium sulfate half hydrate before adding water.

About two hours after mixing, the above hardened materials were crushed, sieved and calcined at slightly above the intended operating temperature of the reactor of 350° C. to 400° C. This serves to only partially dehydrate the calcium sulfate and retain the desired crystalline structure.

The material was then loaded into reaction tube 110, and held in place by quartz wool plugs at each end. Although preliminary testing was done in a vertical orientation, the final work was done with the catalyst held in a horizontal position within the furnace. This eliminated convection currents which occurred outside the reaction tube, and gave more uniform axial temperatures.

An example of the catalytic conversion of a lactate ester to an ester of acrylic acid using the equipment illustrated in FIG. 3 is shown in Table 3 below. The catalyst employed was Plaster-of-Paris solidified in the above manner (including intensive grinding/mixing of the dry components), and in this test 15% by weight of powdered calcium metaphosphate was added as a promoter.

The methyl lactate feed rate as a liquid was 0.5 cc/min. The residence time between the methyl lactate vapor produced and catalyst averaged 10 seconds. The test was run for 31.3 hours. The product was sampled every 40 minutes. The temperature maintained in the reactor was held at between 350° C. to 404° C. It was increased as necessary up to a maximum of 404° C. to maintain approximately 50% methyl lactate conversion, as catalyst activity began to diminish at about 8 hours.

TABLE 3

Composition of Liquid Product

| | Average | Range[1] Low | High |
|---|---|---|---|
| Methyl Lactate, Weight % | 49.22 | 32.77 | 57.61 |
| Methyl Acrylate, Weight % | 10.94 | 5.01 | 14.19 |
| Methanol, Weight % | 11.40 | 8.56 | 16.36 |
| Acrylic Acid, Weight % | 10.17 | 4.91 | 19.24 |
| % Recovery (as liquids) | 93.05 | — | — |

[1]The variations in the range column are attributed to the usual problems in experimental determinations involving sampling, analysis and technique.

With a second esterification of the product mixture to convert all of the acrylic acid to the desired product (methyl acrylate), an overall increase in composition to about twenty percent by weight product should be achieved per pass. In terms of methyl acrylate actually produced per unit of methyl lactate consumed, the yield on a molar basis is anticipated to be about 53%.

Among the decomposition products identified were principally acetaldehyde and carbon monoxide. The acetaldehyde is produced in significant amounts probably from the direct decomposition of the methyl lactate, and is recoverable as a valuable by-product. Other gaseous, as well as liquid residues, may be disposed of as boiler fuel.

The reactor configuration for step 70 is expected to be in the form of a stainless steel tube bundle, with the tubes packed with solid catalyst material and surrounded by a vessel containing a heat-transfer medium which may be a condensing vapor, a gas or a liquid. With a condensing vapor the reaction temperature would be controlled by varying the pressure of this heat transfer fluid, which would have the effect of changing its boiling point and hence its condensation temperature.

With a gaseous heat transfer medium, the reactor could be similar to a natural gas reforming furnace in which the tube bundle is heated by a hot combustion gas. In this configuration the temperature would be controlled by conventional combustion control of gaseous or liquid fuel.

Laboratory experiments performed with a stainless steel reactor at pressures of 60 psig and 120 psig increased lactate reaction rates to acrylate esters. However, the formation of polymers from reaction products also increased with these elevated pressures. The net result from such pressure increase was a decrease in product yield. These experiments also revealed that the formation of polymers from reaction products and lactate feed material was accelerated by contact with the stainless steel surfaces of the vaporizer, reactor, and connecting piping. This effect can be avoided by passivating the surfaces in contact with reactants and products with a silating agent, such as hexamethyldisilazane.

Referring again to FIG. 1, the liquid effluent from dehydration step 70 is expected to contain acrylic acid, lactic acid, and other degradation products in addition to the desired acrylate ester. As such, it is re-esterified in the presence of an ion exchange resin and methanol in step 75 to convert the acrylic acid formed by step 70 into the desired acrylate product. Lactic acid would also be esterified for recycle to the dehydration reactor. The esterification reactor of step 75 is expected to comprise vertical columns packed with an acidic ion exchange resin. Amberlyst 15, marketed by the Rohm and Haas Company, is a representative resin of this type. The condensed liquid product from step 75 would be distilled in step 80. Distillation step 80 would comprise two multiple plate fractional distillation columns; the first to recover alcohol for recycle (stream 85) and the second for product finishing to meet required quality specifications.

It will be apparent that the above conversion of the lactic acid ester in accordance with the invention may be useful in other processes having nothing to do with fermentation, or ammonium lactate production or chemistry.

Lactic Acid Production

In accordance with another aspect of the invention, it would also be possible to produce highly purified forms of lactic acid from the intermediate production of lactic acid ester.

Purified lactic acid would be producible directly from the lactic acid ester produced from the $CO_2$ catalysis of an ammonium lactate and alcohol solution. The recovered lactic acid ester solution would be concentrated or purified, and then hydrolyzed back into lactic acid and the alcohol, with the lactic acid then recovered.

This could be conducted catalytically with an acid ion exchange resin under a variety of easily maintained conditions of modest temperatures and pressures. In this aspect of the invention, the purified lactate ester would be combined with water, as necessary, heated to a temperature in the range of 100° C. to 150° C. at slightly above atmospheric pressure, and passed through a reactor containing a bed of ion exchange resin in highly acidified form. The Amberlyst 15 resin mentioned for esterification step 75 above would also be a suitable catalyst for lactic acid ester hydrolysis. The resin would promote the hydrolysis of the ester without need for regeneration. In conventional acid hydrolysis, with for example sulfuric acid, the product would need to be treated to remove the contaminating catalyst. However, by use of an acid in the form of an ion exchange resin, the acid would be fixed and immobile, and would function without being in a soluble form. As such, the catalyst won't contaminate the product, which would otherwise require another purification process. The resulting alcohol should be readily removed from the reactor for recycle, as a vapor assuming a methyl lactate feed, or by simple distillation of the product for higher alcohol lactate esters.

The lactic acid produced in accordance with this aspect of the invention could of course be made from an ammonium lactate feed obtained from other than fermentation processes.

Acrylic Acid Production

In accordance with yet another aspect of the invention, it would also be possible to produce highly purified forms of acrylic acid from an ammonium lactate feed obtained from fermentation or other processes. This could be conducted catalytically with the same highly acidified form of an ion exchange resin such as described immediately above. In this instance, the acrylate ester product from step 80 would be hydrolyzed to acrylic acid by passing through a reactor containing a bed of such resin. The fixed and immobile resin would again provide the advantage of promoting hydrolysis of the ester, here the acrylate, into acid without the need for regeneration. The resulting alcohol could be removed similar to the manner described immediately above.

Alternately, acrylic acid might also be economically extracted from the product stream of dehydration step 70, with the acrylate product also produced being purified and hydrolyzed to acrylic acid as described above.

In compliance with the statute, the invention has been described in language more or less specific as to methodical features. It is to be understood, however, that the invention is not limited to the specific features described, since the means disclosed comprise preferred forms of putting various aspects of the invention into effect. The invention is, therefore, claimed in any of its forms or modifications within the proper scope of the appended claims appropriately interpreted in accordance with the doctrine of equivalents.

We claim:

1. A method of producing esters of lactic acid from fermentable carbohydrate materials comprising the following steps:
    a) fermenting the carbohydrate material with a lactic-acid-forming organism in the presence of $NH_3$ to produce ammonium lactate;
    b) combining the ammonium lactate with an alcohol;
    c) combining the ammonium lactate and alcohol with an effective catalyzing amount of gaseous $CO_2$ to produce a reaction mixture, maintaining the reaction mixture at a predetermined reaction mixture pressure and at a predetermined reaction mixture temperature for a predetermined period of time so as to catalytically esterify the reaction mixture into a lactic acid ester containing solution; and
    d) purifying the lactic acid ester from the lactic acid ester containing solution.

2. The method of claim 1 wherein the reaction mixture pressure is from approximately 1 atmosphere to 200 atmospheres and is sufficient to maintain the ammonium lactate and alcohol in the reaction mixture in the liquid phase.

3. The method of claim 1 wherein the reaction mixture temperature is from approximately 100° C. to 200° C.

4. The method of claim 1 wherein the reaction mixture temperature is from approximately 160° C. to 180° C.

5. The method of claim 1 wherein the period of time is less than or equal to 2 hours.

6. The method of claim 1 wherein the molar ratio of alcohol to ammonium lactate in the reaction mixture is from 1:1 to 10:1, and the effective amount of $CO_2$ is defined by a partial pressure of $CO_2$ in the reaction mixture of from approximately 1 atmosphere to 200 atmospheres.

7. The method of claim 1 wherein,
    the reaction mixture temperature is from approximately 100° C. to 200° C.;
    the reaction mixture pressure is from approximately 1 atmosphere to 200 atmospheres and is sufficient to maintain the ammonium lactate and alcohol in the reaction mixture in the liquid phase;
    the period of time is less than or equal to 2 hours; and
    the molar ratio of alcohol to ammonium lactate in the reaction mixture is from 1:1 to 10:1, and the effective amount of $CO_2$ is defined by a partial pressure of $CO_2$ in the reaction mixture of from approximately 1 atmosphere to 200 atmospheres.

8. The method of claim 1 wherein the alcohol is selected from the group consisting of methanol, ethanol, propanol, and isopropanol.

9. The method of claim 1 wherein the alcohol has four or more carbon atoms.

10. The method of claim 8 wherein the reaction mixture temperature is from approximately 100° C. to 200° C., and the reaction mixture pressure is from approximately 1 atmosphere to 200 atmospheres and is sufficient to maintain the ammonium lactate and alcohol in the reaction mixture in the liquid phase.

11. The method of claim 8 wherein the molar ratio of alcohol to ammonium lactate in the reaction mixture is from 1:1 to 10:1, and the effective amount of $CO_2$ is defined by a partial pressure of $CO_2$ in the reaction mixture of from approximately 1 atmosphere to 200 atmospheres.

12. The method of claim 8 wherein,
    the reaction mixture temperature is from approximately 100° C. to 200° C.;
    the reaction mixture pressure is from approximately 1 atmosphere to 200 atmospheres and is sufficient to maintain the ammonium lactate and alcohol in the reaction mixture in the liquid phase;
    the period of time is less than or equal to 2 hours; and
    the molar ratio of alcohol to ammonium lactate in the reaction mixture is from 1:1 to 10:1, and the effective amount of $CO_2$ is defined by a partial pressure of $CO_2$ in the reaction mixture of from approximately 1 atmosphere to 200 atmospheres.

13. A method of producing esters of acrylic acid from fermentable carbohydrate materials comprising the following steps:
    a) fermenting the carbohydrate material with a lactic-acid-forming organism in the presence of $NH_3$ to produce ammonium lactate;
    b) combining the ammonium lactate with an alcohol;
    c) combining the ammonium lactate and alcohol with an effective catalyzing amount of gaseous $CO_2$ to produce a reaction mixture, maintaining the reaction mixture at a pressure and at a temperature for a period of time so as to catalytically esterify the reaction mixture into a lactic acid ester containing solution; and
    d) vaporizing lactic acid ester and passing the vaporized lactic acid ester through a solid catalyst bed, the solid catalyst bed comprising an effective catalyzing amount of crystalline hydrated and partially calcined calcium sulfate to catalytically convert lactic acid ester into an acrylic acid ester.

14. The method of claim 13 wherein the vaporized lactic acid ester and solid catalyst bed are maintained in contact at a contact temperature and a contact pressure for a residence time, the calcium sulfate of the catalyst bed being prepared by partially calcining it at or above the contact temperature.

15. The method of claim 13 further comprising passing the acrylic acid ester through a solid acid ion exchange resin to hydrolyze the acrylic acid ester into acrylic acid, and purifying and recovering the acrylic acid.

16. The method of claim 13 wherein the calcium sulfate of the catalyst bed is prepared by a process comprising, mixing water with calcium sulfate half hydrate to a molar ratio of water to calcium sulfate half hydrate of from approximately 1.5:1 to 3.0:1 to produce a hydrated mixture;

allowing the hydrated mixture to dry and harden into a set hydrated mixture;

crushing the set hydrated mixture into a crushed hydrated mixture; and calcining the crushed hydrated mixture at a temperature greater than or equal to approximately 350° C. for a sufficient period of time to only partially dehydrate the crushed hydrated mixture.

17. The method of claim 16 wherein the solid catalyst bed further comprises an additive selected from the group consisting of buffering agents and promoters, the additive being present in an amount from approximately 5 to 25 weight percent of the solid catalyst bed.

18. The method of claim 17 wherein the buffering agents and promoters are selected from the group consisting of calcium carbonate, calcium metaphosphate, calcium orthophosphate, calcium pyrophosphate, potassium dihydrogen orthophosphate, and sodium monohydrogen orthophosphate.

19. The method of claim 16 wherein the calcined calcium sulfate is exposed to $SO_3$ at a temperature of about 330° C. for a period less than or equal to approximately 5 hours.

20. The method of claim 14 wherein the contact temperature is from about 350° C. to 410° C.

21. The method of claim 14 wherein the contact pressure is atmospheric.

22. The method of claim 14 wherein the residence time is less than or equal to about 30 seconds.

23. The method of claim 14 wherein the contact temperature is from about 350° C. to 410° C., the contact pressure is atmospheric, and the residence time is less than or equal to about 30 seconds.

24. The method of claim 13 wherein, the vaporized lactic acid ester and solid catalyst bed are maintained in contact at a contact temperature and a contact pressure for a residence time; the contact temperature being from about 350° C. to 410° C., the contact pressure being atmospheric, and the residence time being less than or equal to about 30 seconds;

the calcium sulfate of the catalyst bed is prepared by a process comprising, mixing water with calcium sulfate half hydrate to a molar ratio of water to calcium sulfate half hydrate of from approximately 1.5:1 to 3.0:1 to produce a hydrated mixture;

allowing the hydrated mixture to dry and harden into a set hydrated mixture;

crushing the set hydrated mixture into a crushed hydrated mixture; and calcining the crushed hydrated mixture at a temperature greater than or equal to approximately 350° C. for a sufficient period of time to only partially dehydrate the crushed hydrated mixture; and the solid catalyst bed further comprises an additive selected from the group consisting of buffering agents and promoters, the buffering agents and promoters being selected from the group consisting of calcium carbonate, calcium metaphosphate, calcium orthophosphate, calcium pyrophosphate, potassium dihydrogen orthophosphate, and sodium monohydrogen orthophosphate.

25. The method of claim 13 wherein the alcohol is selected from the group consisting of methanol, ethanol, propanol, and isopropanol.

26. The method of claim 13 wherein the molar ratio of alcohol to ammonium lactate in the reaction mixture is from 1:1 to 10:1, and the effective amount of $CO_2$ is defined by a partial pressure of $CO_2$ in the reaction mixture of from approximately 1 atmosphere to 200 atmospheres.

27. The method of claim 13 wherein, the reaction mixture temperature is from approximately 100° C. to 200° C.;

the reaction mixture pressure is from approximately 1 atmosphere to 200 atmospheres and is sufficient to maintain the ammonium lactate and alcohol in the reaction mixture in the liquid phase;

the period of time is less than or equal to 2 hours; and the molar ratio of alcohol to ammonium lactate in the reaction mixture is from 1:1 to 10:1, and the effective amount of $CO_2$ is defined by a partial pressure of $CO_2$ in the reaction mixture of from approximately 1 atmosphere to 200 atmospheres.

28. The method of claim 25 wherein the vaporized lactic acid ester and solid catalyst bed are maintained in contact at a contact temperature and a contact pressure for a residence time, the calcium sulfate of the catalyst bed being prepared by partially calcining it at or above the contact temperature.

29. The method of claim 28 wherein the contact temperature is from about 350° C. to 410° C., the contact pressure is atmospheric, and the residence time is less than or equal to about 30 seconds.

30. The method of claim 25 wherein the calcium sulfate of the catalyst bed is prepared by a process comprising, mixing water with calcium sulfate half hydrate to a molar ratio of water to calcium sulfate half hydrate of from approximately 1.5:1 to 3.0:1 to produce a hydrated mixture;

allowing the hydrated mixture to dry and harden into a set hydrated mixture;

crushing the set hydrated mixture into a crushed hydrated mixture; and calcining the crushed hydrated mixture at a temperature greater than or equal to approximately 350° C. for a sufficient period of time to only partially dehydrate the crushed hydrated mixture.

31. The method of claim 26 wherein the vaporized lactic acid ester and solid catalyst bed are maintained in contact at a contact temperature and a contact pressure for a residence time, the calcium sulfate of the catalyst bed being prepared by partially calcining it at or above the contact temperature.

32. The method of claim 31 wherein the contact temperature is from about 350° C. to 410° C., the contact pressure is atmospheric, and the residence time is less than or equal to about 30 seconds.

33. The method of claim 26 wherein the calcium sulfate of the catalyst bed is prepared by a process comprising, mixing water with calcium sulfate half hydrate to a molar ratio of water to calcium sulfate half hydrate of from approximately 1.5:1 to 3.0:1 to produce a hydrated mixture;

allowing the hydrated mixture to dry and harden into a set hydrated mixture;

crushing the set hydrated mixture into a crushed hydrated mixture; and calcining the crushed hydrated mixture at a temperature greater than or equal to approximately 350° C. for a sufficient period of time to only partially dehydrate the crushed hydrated mixture.

34. The method of claim 27 wherein the vaporized lactic acid ester and solid catalyst bed are maintained in contact at a contact temperature and a contact pressure for a residence time, the calcium sulfate of the catalyst bed being prepared by partially calcining it at or above the contact temperature.

35. The method of claim 34 wherein the contact temperature is from about 350° C. to 410° C., the contact pressure is atmospheric, and the residence time is less than or equal to about 30 seconds.

36. The method of claim 27 wherein the calcium sulfate of the catalyst bed is prepared by a process comprising, mixing water with calcium sulfate half hydrate to a molar ratio of water to calcium sulfate half hydrate of from approximately 1.5:1 to 3.0:1 to produce a hydrated mixture;

allowing the hydrated mixture to dry and harden into a set hydrated mixture;

crushing the set hydrated mixture into a crushed hydrated mixture; and calcining the crushed hydrated mixture at a temperature greater than or equal to approximately 350° C. for a sufficient period of time to only partially dehydrate the crushed hydrated mixture.

37. A method of producing esters of lactic acid from ammonium lactate comprising the following steps:

a) combining ammonium lactate with an alcohol;

b) combining the ammonium lactate and alcohol with an effective catalyzing amount of gaseous $CO_2$ to produce a reaction mixture, maintaining the reaction mixture at a reaction mixture pressure and at a reaction mixture temperature for a period of time so as to catalytically esterify the reaction mixture into a lactic acid ester containing solution; and c) purifying the lactic acid ester from the lactic acid ester containing solution.

38. The method of claim 37 wherein the reaction mixture pressure is from approximately 1 atmosphere to 200 atmospheres and is sufficient to maintain the ammonium lactate and alcohol in the reaction mixture in the liquid phase.

39. The method of claim 37 wherein the reaction mixture temperature is from approximately 100° C. to 200° C.

40. The method of claim 37 wherein the reaction mixture temperature is from approximately 160° C. to 180° C.

41. The method of claim 37 wherein the period of time is less than or equal to 2 hours.

42. The method of claim 37 wherein the molar ratio of alcohol to ammonium lactate in the reaction mixture is from 1:1 to 10:1, and the effective amount of $CO_2$ is defined by a partial pressure of $CO_2$ in the reaction mixture of from approximately 1 atmosphere to 200 atmospheres.

43. The method of claim 37 wherein, the reaction mixture temperature is from approximately 100° C. to 200° C.;

the reaction mixture pressure is from approximately 1 atmosphere to 200 atmospheres and is sufficient to maintain the ammonium lactate and alcohol in the reaction mixture in the liquid phase;

the period of time is less than or equal to 2 hours; and the molar ratio of alcohol to ammonium lactate in the reaction mixture is from 1:1 to 10:1, and the effective amount of $CO_2$ is defined by a partial pressure of $CO_2$ in the reaction mixture of from approximately 1 atmosphere to 200 atmospheres.

44. The method of claim 37 wherein the alcohol is selected from the group consisting of methanol, ethanol, propanol, and isopropanol.

45. The method of claim 37 wherein the alcohol has four or more carbon atoms.

46. The method of claim 44 wherein the reaction mixture temperature is from approximately 100° C. to 200° C., and the reaction mixture pressure is from approximately 1 atmosphere to 200 atmospheres and is sufficient to maintain the ammonium lactate and alcohol in the reaction mixture in the liquid phase.

47. The method of claim 44 wherein the molar ratio of alcohol to ammonium lactate in the reaction mixture is from 1:1 to 10:1, and the effective amount of $CO_2$ is defined by a partial pressure of $CO_2$ in the reaction mixture of from approximately 1 atmosphere to 200 atmospheres.

48. The method of claim 44 wherein, the reaction mixture temperature is from approximately 100° C. to 200° C.;

the reaction mixture pressure is from approximately 1 atmosphere to 200 atmospheres and is sufficent to maintain the ammonium lactate and alcohol in the reaction mixture in the liquid phase;

the period of time is less than or equal to 2 hours; and the molar ratio of alcohol to ammonium lactate in the reaction mixture is from 1:1 to 10:1, and the effective amount of $CO_2$ is defined by a partial pressure of $CO_2$ in the reaction mixture of from approximately 1 atmosphere to 200 atmospheres.

49. A method of producing lactic acid from fermentable carbohydrate materials comprising the following steps:

a) fermenting the carbohydrate material with a lactic-acid-forming organism in the presence of $NH_3$ to produce ammonium lactate;

b) combining the ammonium lactate with an alcohol;

c) combining the ammonium lactate and alcohol with an effective catalyzing amount of gaseous $CO_2$ to produce a reaction mixture, and maintaining the reaction mixture at a pressure and at a temperature for a period of time so as to esterify the reaction mixture into a lactic acid ester containing solution;

d) purifying the lactic acid ester from the lactic acid ester containing solution;

e) hydrolyzing the lactic acid ester into lactic acid and an alcohol; and f) recovering the lactic acid.

50. The method of claim 49 wherein the reaction mixture pressure is from approximately 1 atmosphere to 200 atmospheres and is sufficient to maintain the ammonium lactate and alcohol in the reaction mixture in the liquid phase.

51. The method of claim 49 wherein the reaction mixture temperature is from approximately 100° C. to 200° C.

52. The method of claim 49 wherein the reaction mixture temperature is from approximately 160° C. to 180° C.

53. The method of claim 49 wherein the period of time is less than or equal to 2 hours.

54. The method of claim 49 wherein the molar ratio of alcohol to ammonium lactate in the reaction mixture is from 1:1 to 10:1, and the effective amount of $CO_2$ is defined by a partial pressure of $CO_2$ in the reaction mixture of from approximately 1 atmosphere to 200 atmospheres.

55. The method of claim 49 wherein,
the reaction mixture temperature is from approximately 100° C. to 200° C.;
the reaction mixture pressure is from approximately 1 atmosphere to 200 atmospheres and is sufficient to maintain the ammonium lactate and alcohol in the reaction mixture in the liquid phase;
the period of time is less than or equal to 2 hours; and
the molar ratio of alcohol to ammonium lactate in the reaction mixture is from 1:1 to 10:1, and the effective amount of $CO_2$ is defined by a partial pressure of $CO_2$ in the reaction mixture of from approximately 1 atmosphere to 200 atmospheres.

56. The method of claim 49 wherein the alcohol is selected from the group consisting of methanol, ethanol, propanol, and isopropanol.

57. The method of claim 49 wherein the alcohol has four or more carbon atoms.

58. The method of claim 49 wherein the step of hydrolyzing the lactic acid ester into lactic acid and an alcohol comprises passing the lactic acid ester through a solid acid ion exchange resin.

59. The method of claim 56 wherein the reaction mixture temperature is from approximately 100° C. to 200° C., and the reaction mixture pressure is from approximately 1 atmosphere to 200 atmospheres and is sufficient to maintain the ammonium lactate and alcohol in the reaction mixture in the liquid phase.

60. The method of claim 56 wherein the molar ratio of alcohol to ammonium lactate in the reaction mixture is from 1:1 to 10:1, and the effective amount of $CO_2$ is defined by a partial pressure of $CO_2$ in the reaction mixture of from approximately 1 atmosphere to 200 atmospheres.

61. The method of claim 56 wherein,
the reaction mixture temperature is from approximately 100° C. to 200° C.;
the reaction mixture pressure is from approximately 1 atmosphere to 200 atmospheres and is sufficient to maintain the ammonium lactate and alcohol in the reaction mixture in the liquid phase;
the period of time is less than or equal to 2 hours; and
the molar ratio of alcohol to ammonium lactate in the reaction mixture is from 1:1 to 10:1, and the effective amount of $CO_2$ is defined by a partial pressure of $CO_2$ in the reaction mixture of from approximately 1 atmosphere to 200 atmospheres.

62. A method of producing lactic acid from ammonium lactate comprising the following steps:
a) combining ammonium lactate with an alcohol;
b) combining the ammonium lactate and alcohol with an effective catalyzing amount of gaseous $CO_2$ to produce a reaction mixture, and maintaining the reaction mixture at a pressure and at a temperature for a period of time so as to esterify the reaction mixture into a lactic acid ester containing solution;
c) purifying the lactic acid ester from the lactic acid ester containing solution;
d) hydrolyzing the lactic acid ester into lactic acid and an alcohol; and
e) recovering the lactic acid.

63. The method of claim 62 wherein the reaction mixture pressure is from approximately 1 atmosphere to 200 atmospheres and is sufficient to maintain the ammonium lactate and alcohol in the reaction mixture in the liquid phase.

64. The method of claim 62 wherein the reaction mixture temperature is from approximately 100° C. to 200° C.

65. The method of claim 62 wherein the reaction mixture temperature is from approximately 160° C. to 180° C.

66. The method of claim 62 wherein the period of time is less than or equal to 2 hours.

67. The method of claim 62 wherein the molar ratio of alcohol to ammonium lactate in the reaction mixture is from 1:1 to 10:1, and the effective amount of $CO_2$ is defined by a partial pressure of $CO_2$ in the reaction mixture of from approximately 1 atmosphere to 200 atmospheres.

68. The method of claim 62 wherein,
the reaction mixture temperature is from approximately 100° C. to 200° C.;
the reaction mixture pressure is from approximately 1 atmosphere to 200 atmospheres and is sufficient to maintain the ammonium lactate and alcohol in the reaction mixture in the liquid phase;
the period of time is less than or equal to 2 hours; and
the molar ratio of alcohol to ammonium lactate in the reaction mixture is from 1:1 to 10:1, and the effective amount of $CO_2$ is defined by a partial pressure of $CO_2$ in the reaction mixture of from approximately 1 atmosphere to 200 atmospheres.

69. The method of claim 62 wherein the alcohol is selected from the group consisting of methanol, ethanol, propanol, and isopropanol.

70. The method of claim 62 wherein the alcohol has four or more carbon atoms.

71. The method of claim 62 wherein the step of hydrolyzing the lactic acid ester into lactic acid and an alcohol comprises passing the lactic acid ester through a solid acid ion exchange resin.

72. The method of claim 69 wherein the reaction mixture temperature is from approximately 100° C. to 200° C., and the reaction mixture pressure is from approximately 1 atmosphere to 200 atmospheres and is sufficient to maintain the ammonium lactate and alcohol in the reaction mixture in the liquid phase.

73. The method of claim 69 wherein the molar ratio of alcohol to ammonium lactate in the reaction mixture is from 1:1 to 10:1, and the effective amount of $CO_2$ is defined by a partial pressure of $CO_2$ in the reaction mixture of from approximately 1 atmosphere to 200 atmospheres.

74. The method of claim 69 wherein,
the reaction mixture temperature is from approximately 100° C. to 200° C.;
the reaction mixture pressure is from approximately 1 atmosphere to 200 atmospheres and is sufficient to maintain the ammonium lactate and alcohol in the reaction mixture in the liquid phase;
the period of time is less than or equal to 2 hours; and
the molar ratio of alcohol to ammonium lactate in the reaction mixture is from 1:1 to 10:1, and the effective amount of $CO_2$ is defined by a partial pressure of $CO_2$ in the reaction mixture of from approximately 1 atmosphere to 200 atmospheres.

75. A method of producing esters of acrylic acid from fermentable carbohydrate materials comprising the following steps:
   a) fermenting the carbohydrate material with a lactic-acid-forming organism in the presence of $NH_3$ to produce ammonium lactate;
   b) combining the ammonium lactate with an alcohol;
   c) esterifying the ammonium lactate and alcohol into a lactic acid ester; and
   d) catalyzing conversion of the lactic acid ester by vaporizing the lactic acid ester and passing the vaporized lactic acid ester through a solid catalyst bed, the solid catalyst bed comprising an effective catalyzing amount of crystalline hydrated and partially calcined calcium sulfate to catalytically convert lactic acid ester into an acrylic acid ester, the calcium sulfate of the catalyst bed being prepared by a process comprising:
      mixing water with calcium sulfate half hydrate to a molar ratio of water to calcium sulfate half hydrate of from approximately 1.5:1 to 3.0:1 to produce a hydrated mixture;
      allowing the hydrated mixture to dry and harden into a set hydrated mixture;
      crushing the set hydrated mixture into a crushed hydrated mixture;
      calcining the crushed hydrated mixture at a temperature greater than or equal to approximately 350° C. for a sufficient period of time to only partially dehydrate the crushed hydrated mixture; and
      the calcined calcium sulfate being exposed to $SO_3$ at a temperature of about 330° C. for a period less than or equal to approximately 5 hours.

76. A method of producing esters of acrylic acid from lactic acid esters comprising:
   vaporizing a lactic acid ester; and
   passing the vaporized lactic acid ester through a solid catalyst bed, the solid catalyst bed comprising an effective catalyzing amount of crystalline hydrated and partially calcined calcium sulfate to catalytically convert lactic acid ester into an acrylic acid ester, the calcium sulfate of the catalyst bed being prepared by a process comprising:
      mixing water with calcium sulfate half hydrate to a molar ratio of water to calcium sulfate half hydrate of from approximately 1.5:1 to 3.0:1 to produce a hydrated mixture;
      allowing the hydrated mixture to dry and harden into a set hydrated mixture;
      crushing the set hydrated mixture into a crushed hydrated mixture;
      calcining the crushed hydrated mixture at a temperature greater than or equal to approximately 350° C. for a sufficient period of time to only partially dehydrate the crushed hydrated mixture; and
      the calcined calcium sulfate being exposed to $SO_3$ at a temperature of about 330° C. for a period less than or equal to approximately 5 hours.

* * * * *